(12) United States Patent
Yoshimoto et al.

(10) Patent No.: US 8,357,770 B2
(45) Date of Patent: Jan. 22, 2013

(54) OLIGOANILINE COMPOUND AND USE THEREOF

(75) Inventors: Takuji Yoshimoto, Funabashi (JP); Taku Kato, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 454 days.

(21) Appl. No.: 12/441,111

(22) PCT Filed: Sep. 5, 2007

(86) PCT No.: PCT/JP2007/067277
§ 371 (c)(1),
(2), (4) Date: Mar. 12, 2009

(87) PCT Pub. No.: WO2008/032617
PCT Pub. Date: Mar. 20, 2008

(65) Prior Publication Data
US 2009/0270585 A1 Oct. 29, 2009

(30) Foreign Application Priority Data
Sep. 13, 2006 (JP) ................................. 2006-247605

(51) Int. Cl.
*C08G 69/26* (2006.01)
(52) U.S. Cl. ........................................ 528/332; 528/397
(58) Field of Classification Search .................. 528/332, 528/397
See application file for complete search history.

(56) References Cited

U.S. PATENT DOCUMENTS
6,235,871 B1    5/2001    Singer et al.
(Continued)

FOREIGN PATENT DOCUMENTS
EP    1589788 A1    10/2005
(Continued)

OTHER PUBLICATIONS
Fumanashi et al (JP2003-313547), machine translation.*
(Continued)

*Primary Examiner* — Gregory Listvoyb
(74) *Attorney, Agent, or Firm* — Birch, Stewart, Kolasch & Birch, LLP

(57) ABSTRACT

Disclosed is an oligoaniline compound represented by the formula (1), (2), (3) or (4) below, which exhibits high solubility in a low-polarity solvent. This oligoaniline compound is suitable as a charge-transporting material which enables to realize excellent device characteristics such as low driving voltage when applied to an OLED device.

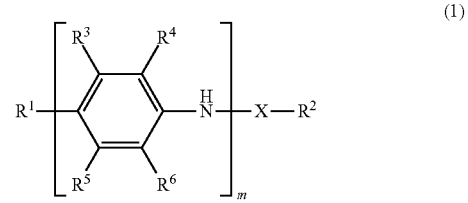

(1)

(2)

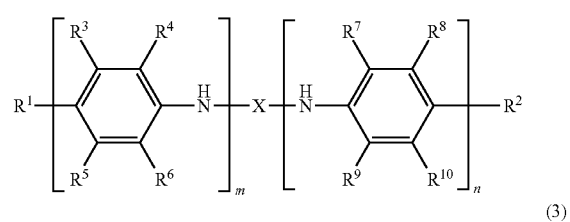

(3)

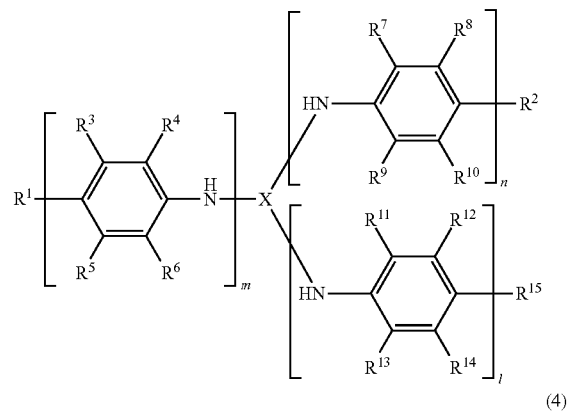

(4)

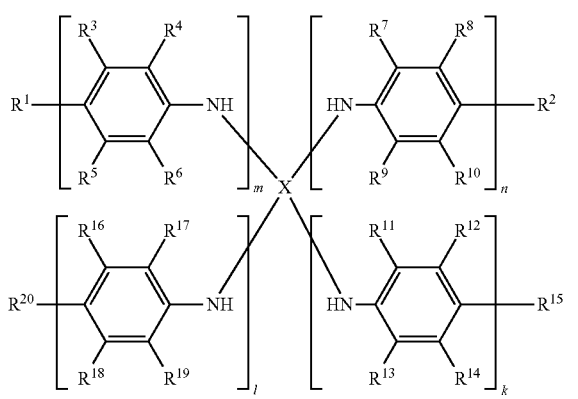

(In the formulae, $R^1$-$R^{20}$ independently represent a hydrogen atom, a halogen atom, a hydroxy group, an amino group, a silanol group, a thiol group, a carboxyl group, a sulfonic acid group, a phosphate group, a phosphoric acid ester group, an ester group, a thioester group, an amide group, a nitro group, a monovalent hydrocarbon group, an organoxy group, an organoamino group, an organosilyl group, an organothio group, an acyl group or a sulfonic group; m, n, l and k independently represent an integer respectively satisfying $1 \leq m \leq 20$, $1 \leq n \leq 20$, $1 \leq l \leq 20$ and $1 \leq k \leq 20$; and X represents a fluorinated aryl group).

13 Claims, No Drawings

U.S. PATENT DOCUMENTS

2005/0221124 A1    10/2005    Hwang et al.

FOREIGN PATENT DOCUMENTS

| | | |
|---|---|---|
| EP | 1640372 A1 | 3/2006 |
| EP | 1 840 130 A1 | 10/2007 |
| JP | 56-155939 A | 12/1981 |
| JP | 3-273087 A | 12/1991 |
| JP | 6-181463 A | 6/1994 |
| JP | 10-316871 A | 12/1998 |
| JP | 2000-204158 A | 7/2000 |
| JP | 2001-226331 A | 8/2001 |
| JP | 2002-151272 A | 5/2002 |
| JP | 2003-313547 A | 11/2003 |
| JP | 2005-108828 A | 4/2005 |
| JP | 2005-116247 A | 4/2005 |
| JP | 2006-273791 A | 10/2006 |
| WO | WO 99/28290 A1 | 6/1999 |
| WO | WO-03/050201 A1 | 6/2003 |
| WO | WO-2004/043117 A1 | 5/2004 |
| WO | WO-2005/043962 A1 | 5/2005 |
| WO | WO 2005/056638 A1 | 6/2005 |
| WO | WO-2005/107335 A1 | 11/2005 |
| WO | WO-2006/025342 A1 | 3/2006 |
| WO | WO-2006/078021 A1 | 7/2006 |

OTHER PUBLICATIONS

Slyke et al., "Organic electroluminescent devices with improved stability" Applied Physics Letters, vol. 69 (15), Oct. 7, 1996, pp. 2160-2162.

Gustafsson et al., "Flexible light-emitting diodes made from soluble conducting polymers" Nature, vol. 357, Jun. 11, 1992, pp. 477-479.

Bharathan et al., "Polymer electroluminescent devices processed by inkjet printing: I. Polymer light-emitting logo" Applied Physics Letters, 1998, vol. 72, pp. 2660-2662.

Zhang et al., "Synthesis of Oligomeric Anilines" Synthetic Metals, 1997, vol. 84, pp. 119-120.

Ochi et al., "Preparation of Linear Oligoaniline Derivatives Using Titanium Alkoxide as a Condensing Agent" Bulletin of Chemical Society of Japan, 1994, vol. 67, pp. 1749-1752.

Extended European Search Report dated Jan. 11, 2010 for corresponding European Application No. 07806720.4.

* cited by examiner

OLIGOANILINE COMPOUND AND USE THEREOF

TECHNICAL FIELD

This invention relates to an oligoaniline compound and use thereof and more particularly, to an oligoaniline compound containing a fluorinated aryl group and the use of the compound as a charge-transporting material. The fields of use include a varnish including the compound, a charge-transporting thin film obtained by use of the varnish, and an organic electroluminescent (hereinafter abbreviated as organic EL) device using the charge-transporting thin film, and the like.

BACKGROUND ART

It has been reported that with low molecular weight organic EL (hereinafter abbreviated as OLED) devices, provision of a copper phthalocyanine (CuPC) layer as a hole injection layer enables the drive voltage to be lowered and initial characteristics, such as an luminous efficiency, to be improved and also a life characteristic to be improved (Non-Patent Document 1: Applied Physics Letters, United States of America, 1996, Vol. 69, p. 2160-2162).

On the other hand, it has also been reported that with organic EL (hereinafter abbreviated as PLED) devices using polymer light-emitting materials, when thin films made of polyaniline materials (Patent Document 1: JP-A 3-273087, Non-Patent Document 2: Nature, Britain, 1992, Vol. 357, p. 477-479) and polythiophene materials (Non-Patent Document 3: Applied Physics Letters, United States of America, 1998, Vol. 72, p. 2660-2662) are used as a hole-transporting layer, similar results as in the OLED device are obtained.

In recent years, it has been reported that charge-transporting varnishes have been found, which are made of homogeneous solutions obtained by completely dissolving low molecular weight oligoaniline materials or oligothiophene materials of high solubility in organic solvents. When the hole injection layer obtained from the varnish is inserted into an organic EL device, a flattening effect of an underlying substrate and excellent EL device characteristics are obtained (Patent Document 2: JP-A 2002-151272, Patent Document 3: WO 2005/043962 Pamphlet.

The low molecular weight oligomer compound per se is low in viscosity, for which where an ordinary organic solvent is used, a process margin in film-forming operations becomes narrow, thus making it difficult to form a film having high uniformity when using a variety of coating processes such as spin coating, ink jet coating, spray coating and the like and various baking conditions. However, the use of different types of solvents to be added enables the viscosity, boiling point and vapor pressure to be controlled and thus, it becomes possible to obtain a film surface having high uniformity in correspondence with different types of coating processes (Patent Document 4: WO 2004/043117 Pamphlet, Patent Document 5: WO 2005/107335 Pamphlet).

The reason why no solid precipitation takes place irrespective of the addition of a variety of solvents as set out above and the solution is kept uniform is due to the high solubility and non-agglutinative nature of the low molecular weight oligomer compound. Accordingly, the solubility characteristics of coating-type charge-transporting materials are very important.

In recent years, in view of the problems involved in the solvent resistance of ink jet coating apparatus and the solvent resistance characteristic of structures on substrates such as an insulating film, a partition wall and the like, there has been demanded coating with a charge-transporting varnish, especially, using a low-polarity solvent.

Non-Patent Document 1: Applied Physics Letters, USA, 1996, Vol. 69, p. 2160-2162

Non-Patent Document 2: Nature, UK, 1992, Vol. 357, p. 477-479

Non-Patent Document 3: Applied Physics Letters, USA, 1998, Vol. 72, p. 2660-2662

Patent Document 1: JP-A 3-273087

Patent Document 2: JP-A 2002-151272

Patent Document 3: WO 2005/043962 Pamphlet

Patent Document 4: WO 2004/043117 Pamphlet

Patent Document 5: WO 2005/107335 Pamphlet

DISCLOSURE OF THE INVENTION

Problems to be Solved by the Invention

The invention has been made under these circumstances in the art and has for its object the provision of an oligoaniline compound suited as a charge-transporting material, which exhibits high solubility in low-polarity solvents and is able to realize excellent device characteristics, such as a low drive voltage and the like when applied to an OLED device.

Means for Solving the Problems

We made intensive studies in order to achieve the above object and, as a result, found that a fluorinated aryl-bearing oligoaniline represented by the following formulas (1) to (4) exhibits high solubility in low-polarity solvents and high charge transportability when used in combination with charge-accepting materials and is able to reduce a drive voltage of an OLED device when used as a hole injection layer of the device, thereby arriving at completion of the invention.

More particularly, the invention provides:

1. An oligoaniline compound, characterized by being represented by the formula (1), (2), (3) or (4)

[Chemical Formula 1]

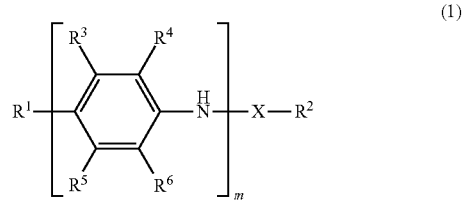

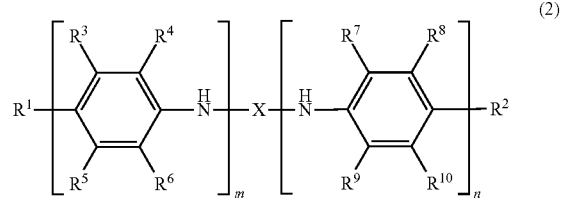

-continued

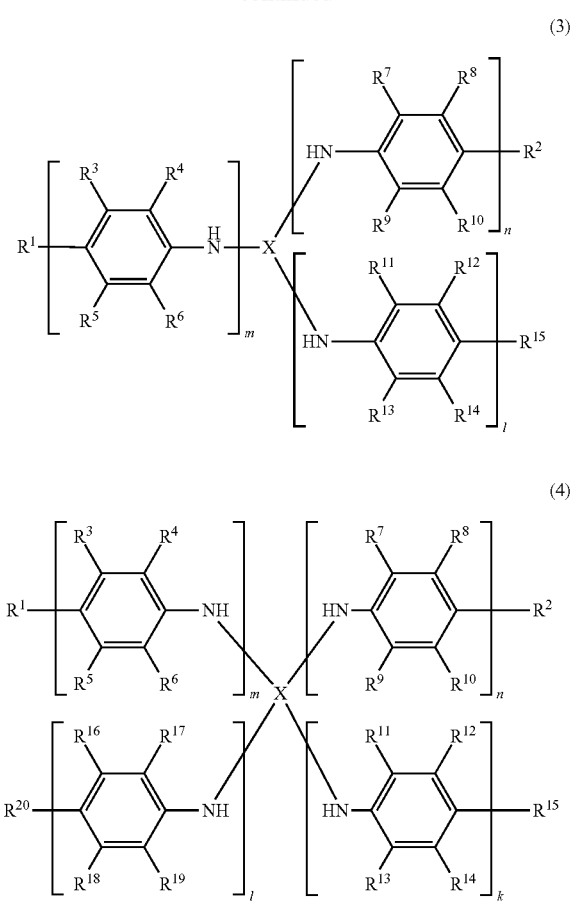

(wherein $R^1$ to $R^{20}$ independently represent a hydrogen atom, a halogen atom, a hydroxyl group, an amino group, a silanol group, a thiol group, a carboxyl group, a phosphate group, a phosphoric acid ester group, an ester group, a thioester group, an amide group, a nitro group, a monovalent hydrocarbon group, an organoxy group, an organoamino group, an organosilyl group, an organothio group, an acyl group or a sulfone group, m, n, l and k are, respectively, such integers that $1 \leq m \leq 20$, $1 \leq n \leq 20$, $1 \leq l \leq 20$ and $1 \leq k \leq 20$ are satisfied, and X represents a fluorinated aryl group);

2. An oligoaniline compound wherein a primary and/or secondary amino group existing in the compound represented by the formula (1), (2), (3) or (4) is intermolecularly added to the fluorinated aryl group of the compound represented by the formula (1), (2), (3) or (4)

[Chemical Formula 2]

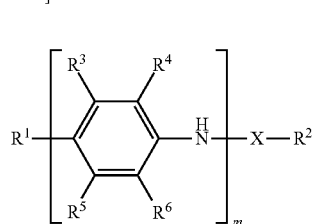

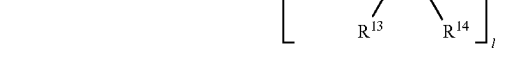

(wherein $R^1$ to $R^{20}$ independently represent a hydrogen atom, a halogen atom, a hydroxyl group, an amino group, a silanol group, a thiol group, a carboxyl group, a phosphate group, a phosphoric acid ester group, an ester group, a thioester group, an amide group, a nitro group, a monovalent hydrocarbon group, an organoxy group, an organoamino group, an organosilyl group, an organothio group, an acyl group or a sulfone group, m, n, l and k are, respectively, such integers that $1 \leq m \leq 20$, $1 \leq n \leq 20$, $1 \leq l \leq 20$ and $1 \leq k \leq 20$ are satisfied, and X represents a fluorinated aryl group);

3. The oligoaniline compound of 1 or 2, wherein X is a fluorinated biphenyl group, a fluorinated phenyl group, a fluorinated binaphthyl group or a fluorinated napthyl group;

4. The oligoaniline compound of 1 or 2, wherein X is a perfluorobiphenyl-derived group, a perfluorobenzene-derived group, a perfluorobinaphthyl-derived group or a perfluoronaphthalene-derived group.

5. A charge-transporting varnish comprising the oligoaniline compound of 1 or 2;

6. A charge-transporting thin film comprising the oligoaniline compound of 1 or 2;

7. A charge-transporting thin film formed from the charge-transporting varnish of 5;

8. An organic electroluminescent device including the charge-transporting thin film of 6 or 7; and 9. A solar cell comprising the charge-transporting thin film of 6 or 7.

Effect of the Invention

The fluorinated aryl group-bearing oligoaniline compounds of the invention exhibit high solubility in various types of organic solvents including low-polarity solvents. Accordingly, a low-polarity organic solvent-based charge-transporting varnish can be prepared by applying a low-polarity solvent partly or wholly to a charge-transporting material containing the oligoaniline compound and a charge-accepting material.

When using this low-polarity organic solvent-based charge-transporting varnish, an ink jet coating apparatus involving a problem on solvent resistance can be used. Moreover, in case where there is a structure on a substrate, such as an insulating film or a partition plate, which involves a problem on solvent resistance, there can be formed an amorphous solid thin film having high flatness without problems.

The resulting thin film exhibits high charge transportability, for which when the film is used as a hole injection layer or hole-transporting layer, the drive voltage of an organic EL device can be lowered.

Further, using the high flatness and high charge transportability of the thin film, the film can be applied as a hole-transporting layer of solar cells, an electrode for fuel cells, a capacitor electrode protective film or an antistatic film.

BEST MODE FOR CARRYING OUT THE INVENTION

The invention is described in more detail.

In the oligoaniline compounds represented by the formulas (1), (2), (3) and (4), $R^1$ to $R^{20}$ independently represent a hydrogen atom, a halogen atom, a hydroxyl group, an amino group, a silanol group, a thiol group, a carboxyl group, a phosphate group, a phosphoric acid ester group, an ester group, a thioester group, an amide group, a nitro group, a monovalent hydrocarbon group, an organoxy group, an organoamino group, an organosilyl group, an organothio group, an acyl group or a sulfone group.

The halogen atoms include chlorine, bromine, fluorine and iodine atoms.

The monovalent hydrocarbon groups include: an alkyl group such as a methyl group, an ethyl group, a propyl group, a butyl group, a t-butyl group, a hexyl group, an octyl group, a decyl group or the like; a cycloalkyl group such as a cyclopentyl group, a cyclohexyl group or the like; a bicycloalkyl group such as a bicyclohexyl group or the like; an alkenyl group such as a vinyl group, a 1-propenyl group, a 2-propenyl group, an isopropenyl group, a 1-methyl-2-propenyl group, a 1, 2 or 3-butenyl group, a hexenyl group or the like; an aryl group such as a phenyl group, a xylyl group, a tolyl group, a biphenyl group, a naphthyl group or the like; and an aralkyl group such as a benzyl group, a phenylethyl group, a phenylcyclohexyl group or the like.

It will be noted that part or the whole of hydrogen atoms of these monovalent hydrocarbon groups may be substituted with a hydroxyl group, a halogen atom, an amino group, a silanol group, a thiol group, a carboxyl group, a sulfone group, a phosphate group, a phosphoric acid ester group, an ester group, a thioester group, an amide group, a nitro group, an organoxy group, an organoamino group, an organosilyl group, an organothio group, an acyl group, an alkyl group, a cycloalkyl group, a bicycloalkyl group, an alkenyl group, an aryl group, an aralkyl group or the like.

The organoxy groups include an alkoxy group, an alkenyloxy group, an aryloxy group and the like, in which the alkyl group, alkenyl group and aryl group thereof may be those mentioned with respect to the above monovalent hydrocarbon group.

The organoamino groups include an alkylamino group such as a phenylamino group, a methylamino group, an ethylamino group, a propylamino group, a butylamino group, a pentylamino group, a hexylamino group, a heptylamino group, an octylamino group, a nonylamino group, a decylamino group, a laurylamino group or the like; a dialkylamino group such as a dimethylamino group, a diethylamino group, a dipropylamino group, a dibutylamino group, a dipentylamino group, a dihexylamino group, a diheptylamino group, an dioctylamino group, a dinonylamino group, a didecylamino group or the like; and a cyclohexylamino group, a morpholino group or the like.

The organosilyl groups include a trimethylsilyl group, a triethylsilyl group, a tripropylsilyl group, a tributylsilyl group, a tripentylsilyl group, a trihexylsilyl group, a pentyldimethylsilyl group, a hexyldimethylsilyl group, an octyldimethylsilyl group, a decyldimethylsilyl group and the like.

The organothio groups include alkylthio groups such as a methylthio group, an ethylthio group, a propylthio group, a butylthio group, a pentylthio group, a hexylthio group, a heptylthio group, an octylthio group, a nonylthio group, a decylthio group, a laurylthio group and the like.

The acyl groups include a formyl group, an acetyl group, a propionyl group, a butyryl group, an isobutyryl group, a valeryl group, an isovaleryl group, a benzoyl group and the like.

The phosphoric acid ester groups include —P(O)(OQ$^1$)(OQ$^2$).

The ester groups include —C(O)OQ$^1$ and —OC(O)Q$^1$.

The thioester groups include —C(S)OQ$^1$ and —OC(S)Q$^1$.

The amide groups include —C(O)NHQ$^1$, —NHC(O)Q$^1$, —C(O)NQ$^1$Q$^2$, and —NQ$^1$C(O)Q$^2$.

In the above formulas, Q$^1$ and Q$^2$, respectively, represent an alkyl group, an alkenyl group or an aryl group, and these groups may be similar to those exemplified with respect to the above monovalent hydrocarbon group.

Although the number of carbon atoms in the monovalent hydrocarbon group, organoxy group, organoamino group, organosilyl group, organothio group, acyl group, phosphoric acid ester group, ester group, thioester group, amide group and the like is not critical, the number of carbon atoms generally ranges 1 to 20, preferably 1 to 8.

Of the substituent groups mentioned above, the fluorine atom, sulfone group, substituted or unsubstituted organoxy group, alkyl group and organosilyl group are more preferred.

It will be noted that "unsubstituted" means bonding of a hydrogen atom. In the afore-indicated substituent groups, a cyclic moiety wherein substituent groups are mutually bonded together may be contained.

X is a fluorinated aryl group. Although no limitation is placed on the aryl group, mention is made of biphenyl, phenyl, binaphthyl, naphthyl, anthracene, naphthacene, terphenyl, tetraphenyl, pyridyl, bipyridyl, thiophene, bithiophene, pyrrole, bipyrrole, furan, bifuran, carbazole, phenanthroline, pyrene, quinoline, iso-quinoline, pyridazine, pyrimidine, purine, acridine, pyrazine, quinoxaline, quinazoline, phthalazine, indole, benzofuran, benzothiophene, pyrazole, isoxazole, isothiazole, indazole, benzoisoxazole, benzisothiazole, imidazole, oxazole, thiazole, benzimidazole, benzoxazole, benzthiazole and the like. Of these, biphenyl, phenyl, binaphthyl and naphthyl groups are preferred.

These aryl groups may be those wherein at least one hydrogen atom of the ring is replaced by a fluorine atom. The hydrogen atoms, not substituted with a fluorine atom, may be substituted with other substituent group. Nevertheless, in order to improve the solubility of the oligoaniline compound in a low-polarity solvent, it is better that all hydrogen atoms on the ring are substituted with a fluorine atom. In this sense, a perfluoroaryl-derived group is preferred. Accordingly, a perfluorobiphenyl-derived group, a perfluorobenzene-derived group, perfluorobinaphthyl-derived group or a perfluoronaphthalene-derived group are most suitable.

Specific examples of other substituent groups include, as used independently, a hydroxyl group, a chlorine atom, a bromine atom, an iodine atom, an amino group, a silanol group, a thiol group, a carboxyl group, a phosphate group, a phosphoric acid ester group, an ester group, a thioester group, an amide group, a nitro group, a monovalent hydrocarbon group, an organoxy group, an organoamino group, an organosilyl group, an organothio group, an acyl group, a sulfone group and the like.

m, n, l and k, respectively, indicate the number of repeating units of a phenylamino group and may be such an integer that $1 \leq m \leq 20$, $1 \leq n \leq 20$, $1 \leq l \leq 20$ and $1 \leq k \leq 20$ are, respectively, satisfied. It is preferred that m, n, l and k are, respectively, at 2 to 8, more preferably at 3 to 5.

In the formula (2), $m+n \leq 40$ should preferably be satisfied, $4 \leq m+n \leq 16$ should more preferably satisfied, and $6 \leq m+n \leq 10$ should most preferably be satisfied.

In the formula (3), $m+n+l \leq 60$ should preferably be satisfied, $6 \leq m+n+l \leq 24$ should more preferably be satisfied, and $9 \leq m+n+l \leq 15$ should most preferably be satisfied.

In the formula (4), $m+n+l+k \leq 80$ should preferably be satisfied, $8 \leq m+n+l+k \leq 32$ should more preferably be satisfied, and $12 \leq m+n+l+k \leq 20$ should most preferably be satisfied.

The control within these ranges makes it easy to secure good solubility in various types of solvents while showing good charge transportability.

It is preferred from the standpoint of enhancing solubility and ensuring uniform charge transportability that the fluorinated aryl group-bearing oligoaniline compounds represented by the formulas (1), (2), (3) and (4) are those oligoaniline compounds wherein there is no molecular weight distribution, or the degree of dispersion is at 1. The molecular weight is generally at 200 or over, preferably at 400 or over as a lower limit in order to suppress volatilization of material and develop charge transportability and is generally at 5000 or below, preferably at 2000 or below as an upper limit for enhancing solubility.

It will be noted that in the oligoaniline compounds of the formulas (1) to (4), the compound may have such a structure that a secondary amino group existing therein and/or a primary amino group, if any, is intermolecularly added to a fluorinated aryl group of another oligoaniline molecule.

The arylsulfonic acid compound represented by the formulas (1) to (4) can be prepared according to the following process.

More particularly, a reagent capable of yielding the fluorinated aryl group X of the afore-indicated formula (1) is acted on an amino group of the following oligoaniline compound (5) or (6). The manner of the reaction is not critical, for which an ordinary nucleophilic substitution reaction can be used, for example.

[Chemical Formula 3]

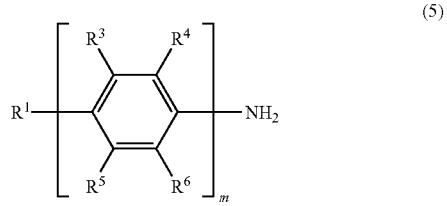

(5)

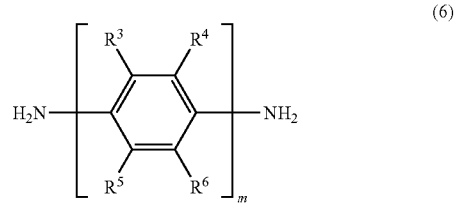

(6)

($R^1$ to $R^6$, respectively, have the same meanings as defined above.)

The (crosslinking) reagent to be reacted with the NH group of the oligoaniline compound (5) or (6) includes, for example, perfluorobiphenyl, perfluorobenzene, perfluorobinaphthyl, perfluoronaphthalene or the like.

It will be noted that when using an aromatic hydrocarbon compound containing three or more fluorine atoms, such a compound serves as a crosslinking reagent and thus, there can be obtained a compound crosslinked with a fluorinated aryl group. When the compound of the formula (5) is subjected to (q−1)-merization by use of a reagent having not smaller than q ($3 \leq q$) fluorine atoms (crosslinking sites), the amount of the reagent is favorably at 1/(q−1) times by mol relative to the compound of the formula (5).

Where the oligoaniline derivative of (5) or (6) and the above-mentioned reagent are reacted with each other, a catalyst may be used. Examples of the catalyst include: bases such as lithium, potassium, lithium hydride, sodium hydride, lithium t-butoxide, sodium t-butoxide, potassium t-butoxide, lithium-diisopropylamide, n-butyl lithium, s-butyl lithium, t-butyl lithium, lithium hexamethyldisilazide, sodium hexamethyldisilazide, potassium hexamethyldisilazide, lithium hydroxide, sodium hydroxide, potassium hydroxide, barium hydroxide, barium oxide, lithium carbonate, sodium carbonate, potassium carbonate, cesium carbonate, calcium carbonate, sodium hydrogen carbonate, triethylamine, diisopropylethylamine, tetramethylethylenediamine, triethylenediamine, pyridine, dimethylaminopyridine, imidazole and the like; and dehydrating condensation agents such as hydrochloric acid, sulfuric acid, diphosphorus pentaoxide, aluminium (III) chloride, boron trifluoride diethyl ether complex, ethyl aluminium dichloride, diethyl aluminium chloride and the like. Of these, sodium hydride, sodium carbonate and potassium carbonate are preferred. The amount of the catalyst is not critical and is preferably in the range of 1.0 to 1.5 times by mol relative to the compound of the formula (5) or (6).

The reaction solvent is preferably an aprotic polar organic solvent and includes, for example, N,N-dimethylformamide (DMF), N,N-dimethylacetamide (DMAc), N-methylpyrrolidone (NMP), 1,3-dimethyl-2-imidazolidinone (DMI), dimethylsulfoxide (DMSO), tetrahydrofuran (THF) dioxane and the like. Of these, dioxane and NMP are preferred.

The possible reaction temperature is generally from −50° C. to a boiling point of a solvent used, preferably within a range of 0 to 140° C. The reaction time is generally at 0.1 to 100 hours.

After completion of the reaction, purification can be made by distilling off the reaction solvent, removing inorganic salts by solid-liquid extraction or liquid-liquid extraction, recrystallization, silica gel column chromatography and the like.

It will be noted that as a result of the reaction, there may be obtained a compound wherein the secondary amino group existing in the reaction product and/or the primary amino group, if any, is intermolecularly added to the fluorinated aryl group of another reaction product.

The charge-transporting varnish according to the invention includes, as a charge-transporting material, an oligoaniline compound represented by the formulas (1) to (4), or an oligoaniline compound obtained by intermolecularly adding a secondary amino group existing in the compound represented by the formula (1), (2), (3) or (4) and/or a primary amino group, if any, to the fluorinated aryl group in the compound represented by the formula (1), (2), (3) or (4).

The charge-transporting varnish is one wherein a charge-transporting material made of the oligoaniline compound of the invention serving as a charge-transporting mechanism body, or a charge-transporting organic material made of this charge-transporting material and an electron or hole-accepting dopant material is dissolved or dispersed in at least one type of solvent.

It will be noted that charge transportability has the same meaning as electric conductivity, meaning hole transportability, electron transportability, and both hole and electron charge transportabilities. The charge-transporting varnish of the invention may be either one that exhibits charge transportability in itself or one that exhibits charge transportability when formed as a solid film obtained from the varnish.

In order to improve the charge transportability and the like of the charge-transporting varnish of the invention, there may be used, if necessary, a charge-accepting dopant material in such a way that an electron-accepting dopant material is used for a hole-transporting material and a hole-accepting dopant material is used for an electron-transporting material. In either case, the materials should preferably have high charge acceptability. With respect to the solubility of the charge-accepting dopant material, the material is not critical in type so far as it is dissolved in at least one solvent used for the varnish.

Specific examples of the electron-accepting dopant material include: an inorganic strong acid such as hydrogen chloride, sulfuric acid, nitric acid, phosphoric acid or the like; Lewis acids such as aluminium (III) chloride ($AlCl_3$), titanium (IV) chloride ($TiCl_4$), boron tribromide ($BBr_3$), boron trifluoride ether complex ($BF_3 \cdot OEt_2$), iron (III) chloride ($FeCl_3$), copper (II) chloride ($CuCl_2$), antimony (V) pentachloride ($SbCl_5$), arsenic (V) pentafluoride ($AsF_5$), phosphorus pentafluoride ($PF_5$), tris(4-bromophenyl)aluminium hexachloroantimonate (TBPAH) or the like; an organic strong acid such as benzenesulfonic acid, tosylic acid, camphorsulfonic acid, hydroxybenzene sulfonic acid, 5-sulfosalicylic acid, dodecylbenzene sulfonic acid, polystyrenesulfonic acid, 1,4-benzodioxanedisulfonic acid derivatives described in WO 2005/000832 Pamphlet, arylsulfonic acid derivatives described in WO 2006/025342 Pamphlet, dinonylnaphthalenesulfonic acid derivatives described in JP-A 2005-108828 or the like; and an organic or inorganic oxidizing agent such as 7,7,8,8-tetracyanoquinodimethane (TCNQ), 2,3-dichloro-5,6-dicyano-1,4-benzoquinone (DDQ), iodine or the like, although not limited thereto.

Preferred electron-accepting dopant materials include those electron-accepting dopant materials made of organic strong acids such as 5-sulfosalicyclic acid, dodecylbenzenesulfonic acid, polystyrensulfonic acid, 1,4-benzodioxanedisulfonic acid derivatives described in WO 2005-000832 Pamphlet, dinonylnaphthalenesulfonic acid derivatives described in JP-A 2005-108828 and the like.

Specific examples of the hole-accepting dopant include alkali metals (Li, Na, K, Cs), and metal complexes such as lithium quinolilate (Liq), lithium acetylacetonate (Li(acac)) and the like although not limited thereto.

The solvent used for preparing the charge-transporting varnish include: water; and organic solvents such as methanol, DMF, DMAC, NMP, DMI, DMSO, chloroform, dichloroethane, toluene and the like. These solvents may be used singly or in admixture of two or more, and the amount can be set at 5 to 100 weight % based on the total amount of solvents used for the varnish.

Since the oligoaniline compound of the invention has high solubility in low-polarity solvents, there may be used, as at least a part of the solvent, a low-polarity solvent such as toluene, xylene, chlorobenzene, dichlorobenzene, trichlorobenzene, dichloroethane, chloroform, dichloromethane or the like.

It is to be noted that the charge-transporting varnish is preferably in a state of being completely dissolved or uniformly dispersed in such a solvent as mentioned above.

The charge-transporting varnish of the invention favorably contains at least one high-viscosity organic solvent that has a viscosity of 10 to 200 mPa·s, preferably 50 to 150 mPa·s at 20° C. and a boiling point of 50 to 300° C., preferably 150 to 250° C., at normal pressures.

The high-viscosity organic solvent is not limited in type and includes, for example, cyclohexanol, ethylene glycol, ethylene glycol diglycidyl ether, 1,3-octylene glycol, diethylene glycol, dipropylene glycol, triethylene glycol, tripropylene glycol, 1,3-butanediol, 2,3-butanediol, 1,4-butanediol, propylene glycol, hexylene glycol and the like.

The ratio of the high-viscosity organic solvent to the total of the solvents used for the varnish of the invention is preferably within such a range that no solid precipitates and the ratio is preferably at 5 to 80 weight % in so far as no solid matter precipitates.

Further, for the purposes of improving wettability to a substrate, controlling the surface tension of a solvent, controlling the polarity and controlling the boiling point, other type of solvent capable of imparting flatness to a film upon baking may be mixed at a ratio of 1 to 90 weight %, preferably 1 to 50 weight %, relative to the total of the solvents used for the varnish.

Such solvents include, for example, butyl cellosolve, diethylene glycol diethyl ether, dipropylene glycol monomethyl ether, ethyl carbitol, diacetone alcohol, γ-butyrolactone, ethyl lactate and the like although not limited thereto.

The charge-transporting varnish set forth hereinabove is coated onto a substrate and the solvent is evaporated to form a charge-transporting thin film on the substrate.

The coating method of the varnish is not limited and mention is made of a dipping method, a spin coating method, a transfer printing method, a roll coating method, a brushing method, an ink jet method, a spraying method and the like.

The evaporation method of a solvent is not limited and the solvent may be evaporated, for example, by use of a hot plate or oven in an appropriate atmosphere, i.e., in air, in an inert gas such as nitrogen or the like or in vacuum. This permits a thin having a uniform film surface to be obtained.

The baking temperature is not limited so far as a solvent can be evaporated and is preferably at 40 to 250° C. In this connection, a temperature change may be made by two or more stages for the purposes of developing highly uniform film-forming properties and permitting the reaction to proceed on a substrate.

The thickness of the charge-transporting thin film is not limited. When used as a charge-injection layer in an organic EL device, the thickness is favorably at 5 to 200 nm. For changing the film thickness, there are some methods including a method wherein a solid concentration is changed in a varnish and a method wherein an amount of a solution to be coated on a substrate is changed.

In order to fabricate an OLED device by use of the change-transporting varnish of the invention, the following materials and the following fabrication method are used although not limited thereto.

An electrode substrate used is preferably cleaned by preliminarily subjecting to liquid cleaning such as with a detergent, an alcohol, pure water or the like. For instance, an anode substrate is preferably subjected, just prior to use, to a surface treatment such as an ozone treatment, an oxygen-plasma treatment or the like. If an anode material is mainly composed of an organic matter, no surface treatment may be carried.

Where a hole-transporting varnish is used for an OLED device, the following method may be mentioned.

The hole-transporting varnish is coated on an anode substrate, followed by evaporation and baking by such methods as mentioned above to form a hole-transporting thin film on the electrode. This is introduced into a vacuum deposition apparatus, followed by successively depositing a hole-transporting layer, an emission layer, an electron-transporting layer, an electron injection layer and a cathode metal to provide an OLED device. In order to control a light-emitting region, a carrier block layer may be provided between arbitrary layers.

As an anode material, transparent electrodes which are typically made of indium tin oxide (ITO) and indium zinc oxide (IZO) are mentioned, and preferred ones are those having subjected to flattening treatment. Alternatively, polythiophene derivatives and polyaniline derivatives having high charge-transportability may also be used.

The materials for forming the hole-transporting layer include triarylamines such as (triphenylamine) dimer derivative (TPD) (α-naphthyldiphenylamine)dimer (α-NPD), [(triphenylamine)dimer]spiro dimer (Spiro-TAD) and the like, star burst amines such as 4,4',4"-tris[3-methylphenyl (phenyl)amino]triphenylamine (m-MTDATA), 4,4',4"-tris[1-naphthyl(phenyl)amino]triphenylamine (1-TNATA) and the like, and oligothiophenes such as 5,5"-bis-{4-[bis-(4-methylphenyl)amino]phenyl}-2,2':5',2"-terthiophene (BMA-3T) and the like.

The materials for forming the emission layer include tris (8-quinolinolato)aluminium (III) ($Alq_3$), bis(8-quinolinolato)zinc(II) ($Znq_2$), bis(2-methyl-8-quinolinolato)(p-phenylphenolato)aluminium (III) (BAlq) and 4,4'-bis(2,2-diphenylvinyl)biphenyl (DPVBi) and the like. The electron-transporting material or hole-transporting material and a light-emitting dopant may be co-deposited thereby forming an emission layer.

The electron-transporting materials include $Alq_3$, BAlq, DPVBi, (2-(4-biphenyl)-5-(4-t-butylphenyl)-1,3,4-oxadiazole) (PBD), a triazole derivative (TAZ), bathocuproine (BCP), silole derivatives and the like.

Light-emitting dopants include quinacridone, rubrene, coumarin 540, 4-(dicyanomethylene)-2-methyl-6-(p-dimethylaminostyryl)-4H-pyran (DCM), tris(2-phenylpyridine) iridium (III) ($Ir(ppy)_3$), (1,10-phenthroline)-tris(4,4,4-trifluoro-1-(2-thienyl)-butan-1,3-dionate)europium (III) (Eu $(TTA)_3$-phen) and the like.

The materials for forming the carrier block layer include PBD, TAZ, BCP and the like.

The materials for forming the electron injection layer include lithium oxide ($LiO_2$), magnesium oxide (MgO), alumina ($Al_2O_3$), lithium fluoride (LiF), magnesium fluoride ($MgF_2$), strontium fluoride ($SrF_2$), Liq, Li(acac), lithium acetate, lithium benzoate and the like.

The cathode materials include aluminium, magnesium-silver alloy, aluminium-lithium alloy, lithium, sodium, potassium, cesium and the like.

Where the electron-transporting varnish is used for an OLED device, the following method can be used.

The electron-transporting varnish is coated onto a cathode substrate to form an electron-transporting thin film, and the film is introduced into a vacuum deposition apparatus, followed by forming an electron-transporting layer, an emission layer, a hole-transporting layer and a hole injection layer by use of such materials as mentioned hereinabove and forming a film of an anode material by a method such as of sputtering to provide an OLED device.

Although a method of making a PLED device by use of the charge-transporting varnish of the invention is not limited, the following method can be mentioned.

In the fabrication of the above-stated OLED device, a light-emitting charge-transporting polymer layer is formed in place of carrying out the vacuum deposition operations of the hole-transporting layer, emission layer, electron-transporting layer and electron injection layer, thereby providing a PLED device including a charge-transporting thin film formed with the charge-transporting varnish of the invention.

More particularly, the charge-transporting varnish (hole-transporting varnish) is coated onto an anode substrate to form a hole-transporting thin film according to such a method as set out hereinabove, on which a light-emitting charge-transporting polymer layer is formed, followed by deposition of a cathode electrode to provide a PLED device.

Alternatively, a charge-transporting varnish (electron-transporting varnish) may be coated onto a cathode substrate to form an electron-transporting thin film according to such a method as set out above, on which a light-emitting charge-transporting polymer layer is formed, followed by further formation of an anode electrode by a method such as of sputtering, deposition, spin coating or the like to provide a PLED device.

The cathode and anode materials used are similar to those used for the fabrication of the OLED device and may be subjected to a similar cleaning treatment and surface treatment.

For the formation of the light-emitting charge-transporting polymer layer, mention is made of a method wherein a light-emitting charge-transporting polymer material or this material to which a light-emitting dopant is added is dissolved or uniformly dispersed in a solvent added thereto, followed by coating onto an electrode substrate on which a hole injection layer has been formed, followed by evaporation of the solvent for film formation.

The light-emitting charge-transporting polymer materials include polyfluorene derivatives such as poly(9,9-dialkylfluorene) (PDAF) and the like, polyphenylenevinylene derivatives such as poly(2-methoxy-5-(2'-ethylhexoxy)-1,4-phenylenevinylene) (MEH-PPV) and the like, polythiophene derivatives such as poly(3-alkylthiophene) (PAT) and the like, polyvinylcarbazole (PVCz), and the like.

The solvents include toluene, xylene, chloroform and the like. The method of the dissolution or uniform dispersion includes a stirring method, a thermal stirring method, a supersonic dispersion method or the like.

The coating method is not limited and includes an ink jet method, a spraying method, a dipping method, a spin coating method, a transfer printing method, a roll coating method, a brushing method or the like. It will be noted that the coating is preferably carried out in an inert gas such as nitrogen, argon or the like.

The evaporation of a solvent is carried out by a method of heating in an oven or on a hot plate in an inert gas or in vacuum.

EXAMPLES

Examples and Comparative Examples are described to more particularly illustrate the invention, and the invention should not be construed as limited to the following Examples. The MS spectrum measuring apparatus used hereinafter is one indicated below.

[MS Spectra]

Apparatus (MALDI-TOF): Voyager-DM™, made by Applied Biosystems Japan, PRO.

Apparatus (FAB): JMS-700T, made by JEOL Ltd.

[1] Preparation of an Oligoaniline Compound

Example 1

According to the following reaction formula, bistetraanilinooctafluorobiphenyl (hereinafter abbreviated as BTAOFB) was prepared from tetraaniline (hereinafter abbreviated as TA) and perfluorobiphenyl (hereinafter abbreviated as PFB). It will be noted that tetraaniline was prepared according to document (Synthetic Metals, 1997, Vol. 84, p. 119-120).

[Chemical Formula 4]

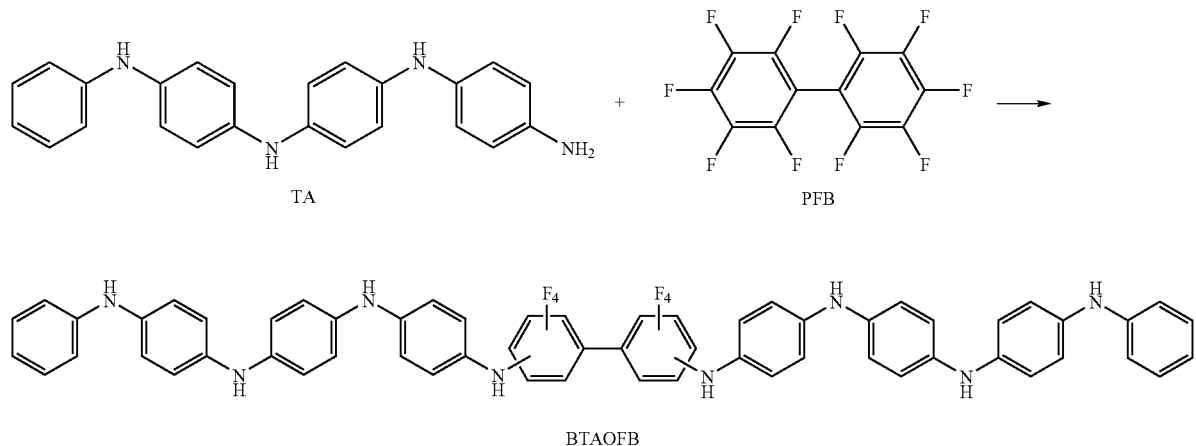

Under nitrogen atmosphere, 500 ml of dehydrated dioxane was added to 5.00 g of TA, 2.73 g of PFB and 2.74 g of 60% sodium hydride, and these were suspended by application of supersonic waves. The resulting purple suspension was heated to 80° C. under nitrogen atmosphere and stirred for 15 hours.

After allowing to cool, the reaction solution was subjected to suction filtration, and the filtrate was washed three times with dioxane, followed by further washing with pure water until the resulting washings reached a pH of 7. The resulting filtrates were combined and concentrated, to which 180 mL of pure water was added, followed by dispersion with ultrasonic waves, suction filtration and washing the resulting filter cake twice with pure water. The filter cake obtained after the washing was dried under reduced pressure and purified with silica gel (190 g of silica gel, eluent: dichloroethane). The resulting distillate was concentrated under reduced pressure and evaporated to dryness to obtain 1.43 g of a greenish black powder.

The thus obtained greenish black powder was subjected to analysis with the MS spectrum measuring apparatus to obtain peaks derived from BTAOFB and the following compound.
LDI-TOF-MS (positive): 1026 [M(BTAOFB)]$^+$,
    1686 [M(the following compound)]$^+$

[Chemical Formula 5]

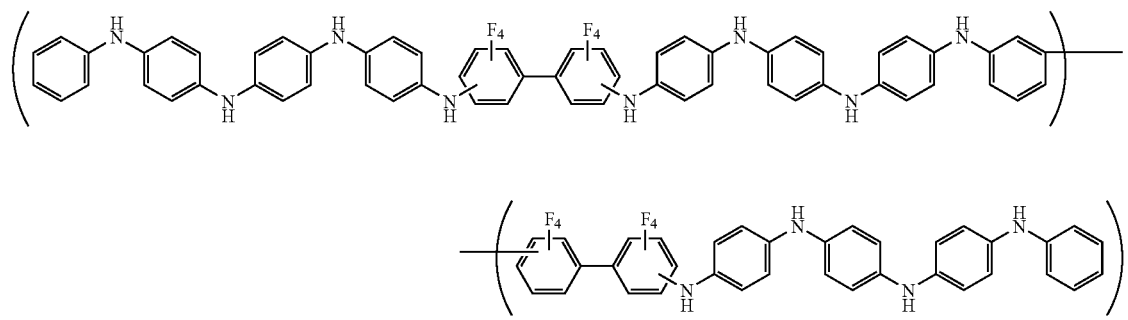

Comparative Example 1

Phenyltetraaniline (hereinafter abbreviated as PTA), which is a fluorinated aryl group-free oligoaniline, was prepared according to the following procedure. More particularly, based on the method described in Bulletin of Chemical Society of Japan, 1994, Vol. 67, p. 1749-1752, PTA was obtained according to the following procedure.

[Chemical Formula 6]

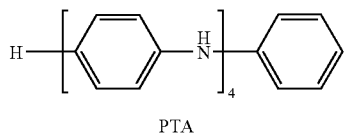

PTA

In 2 liters of toluene, 12.977 g of p-phenylenediamine was dissolved, to which 245.05 g of titanium tetra-n-butoxide serving as a dehydrating condensation agent was added, followed by dissolving it at 70° C. for 30 minutes. Thereafter, 53.346 g of p-hydroxydiphenylamine was added, then the reaction is performed at a temperature of 100° C. for 24 hours under nitrogen atmosphere. After completion of the reaction, the reaction solution was filtered and the resulting filtrate was washed with toluene and then with ether and dried to obtain silver crystals. To the thus obtained crystals, 25 parts by weight of dioxane and 0.2 equivalents of hydrazine monohydrate were added, under which the reaction system was purged with nitrogen, followed by heating under reflux to dissolve the crystals. To the thus obtained solution, 25 parts by weight of toluene relative to the crystals was added to the resulting solution to suspend the crystals. After heating under reflux, 10 parts by weight of dioxane was further added and subjected to heating under reflux to dissolve the crystals, and the resulting solution was subjected to thermal filtration.

The solid matter precipitated from the filtrate was recrystallized and washed under nitrogen atmosphere successively with toluene-dioxane (1:1), and ether, followed by collection with filtration. The resulting crystals were dried under reduced pressure at 60° C. for 10 hours. A similar recrystallization operation was repeated once more to obtain 39.60 g of white crystals (yield: 75%).

BTAOFB and PTA obtained in Example 1 and Comparative Example 1 were checked with respect to the solubility in low-polarity organic solvents.
(1) Solubility in Toluene To 100 mg of BTAOFB, 1 mL of toluene was added and heated to 50° C. and stirred, whereupon it was dissolved. No precipitation of a solid matter was observed upon cooling down to room temperature.

On the other hand, 1 mL of toluene was added to 100 mg of PTA and stirred at 50° C., whereupon it was found that the solid was left undissolved and thus, was not dissolved.
(2) Solubility in Dichloroethane To 100 mg of BTAOFB, 1 mL of dichloroethane was added and heated to 50° C. and stirred, whereupon it was dissolved and no solid precipitation observed upon cooling down to room temperature.

To 100 mg of PTA, 1 mL of dichloroethane was added and stirred at 50° C., whereupon it was found that the solid was left undissolved and thus, was not dissolved.

The above results-revealed that the fluorinated aryl group-bearing BTAOFB is more excellent than such a group-free PTA with respect to the solubility in low-polarity solvents such as toluene and dichloroethane.

[2] Fabrication of Charge-Transporting Varnishes and Charge-Transporting Thin Films

Example 2

Under nitrogen atmosphere, 1.30 mL of DMAc was added to a mixture of 70 mg of BTAOFB and 139 mg of 5-sulfosalicyclic acid dihydride, followed by dissolving them in DMAC, to which 3.86 mL of cyclohexanol, melted by heating to 40° C. was added followed by allowing to cool down to room temperature, thereby obtaining a green transparent solution. The thus obtained solution was filtered through a PTFE filter having a pore diameter of 0.2 μm to obtain a green transparent charge-transporting varnish. It will be noted that no clogging was observed upon filtration.

The thus obtained varnish was coated onto an ITO substrate having subjected to ozone cleaning for 40 minutes according a spin coating method and baked on a hot plate at 200° C. for 1 hour to form a charge-transporting thin film. The thin film was made of a uniform amorphous solid.

Comparative Example 2

To a mixture of 100 mg of PTA and 230 mg of 5-sulfosalicyclic acid dihydride, 1.87 ml of DMAc was added and stirred at room temperature to dissolve the mixture therein then 5.53 ml of cyclohexanol, melted by heating to 40° C. was added and stirred to obtain a greenish black solution. The thus obtained solution was filtered through a PTFE filter having a pore size of 0.2 μm to obtain a greenish black charge-transporting varnish. It will be noted that no clogging was observed upon the filtration.

The varnish was spin-coated onto an ITO substrate having been subjected to ozone cleaning for 40 minutes, baked on a hot plate at 200° C. for 1 hour to form a charge-transporting thin film. The thus obtained thin film was made of a uniform amorphous solid.

The solid concentrations of the varnishes of Examples 2 and Comparative Example 2, and the thicknesses and ionization potentials (Ip) of the thin films are shown in Table 1.

It will be noted that the film thickness and ionization potential were, respectively, measured by use of a photoelectronic spectrometer AC-2, made by Riken Keiki Co., Ltd. The film thickness was measured by use of Surfcorder ET-4000A, made by Kosaka Laboratory Ltd.

TABLE 1

|  | Solid concentration [weight %] | Film thickness [nm] | IP [eV] |
|---|---|---|---|
| Example 2 | 4.1 | 25 | 5.45 |
| Comparative Example 2 | 4.1 | 25 | 5.38 |

[3] Fabrication of an OLED Device

Example 3

After formation of a hole-transporting thin film on an ITO substrate in the same manner as in Example 2, this substrate was introduced into a vacuum deposition apparatus, followed by successive vacuum deposition of α-NPD, Alq$_3$, LiF and Al to provide an OLED device. The film thicknesses were, respectively, at 35 nm, 50 nm, 0.5 nm and 100 nm, for which the vacuum deposition operations were, respectively, carried out after the pressure had reached not higher than $8 \times 10^{-4}$ Pa.

The vacuum deposition rate was at 0.35 to 0.40 nm/second for α-NPD and Alq₃, at 0.015 to 0.025 nm/second for LiF and at 0.2 to 0.4 nm/second for Al. The movements between the vacuum deposition operations were performed in vacuum.

Comparative Example 3

Fabrication of an OLED Device

After formation of a charge-transporting thin film on an ITO substrate in the same manner as in Comparative Example 2, the respective films were vacuum deposited in the same manner as in Example 3 to provide an OLED device.

The characteristics of the devices obtained in Example 3 and Comparative Example 3 are shown together in Table 2.

It will be noted that the characteristics of the OLED devices were measured by use of a measuring device of an organic EL luminous efficiency (EL1003, made by Precise Gauges co., ltd.).

TABLE 2

|  | Film thickness (nm) | Current density (mA/cm²) | Voltage (V) | Luminance (cd/m²) | Current efficiency (cd/A) |
|---|---|---|---|---|---|
| Example 3 | 25 | 5 | 6.6 | 160 | 3.2 |
| Comparative Example 3 | 25 | 5 | 7.0 | 166 | 3.3 |

As shown in Table 2, it will be seen that when comparing the OLED characteristics of Example 3 with those OLED characteristics of Comparative Example 2, the drive voltage is lower and the hole injection characteristic is higher. It will also be seen that the current efficiencies are almost equal to each other.

The invention claimed is:

1. An oligoaniline compound, characterized by being represented by the formula (1), (2), (3) or (4)

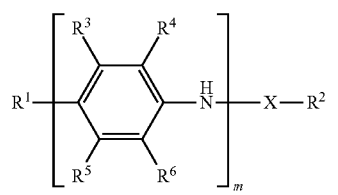

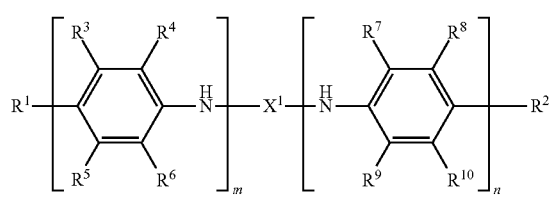

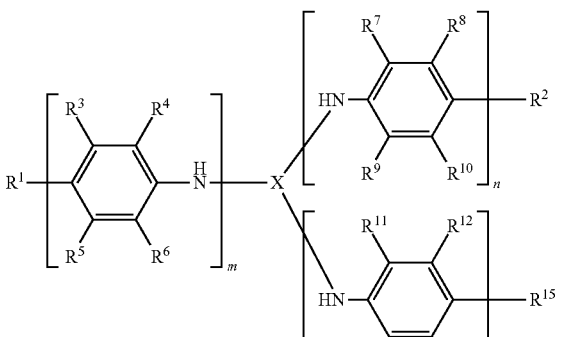

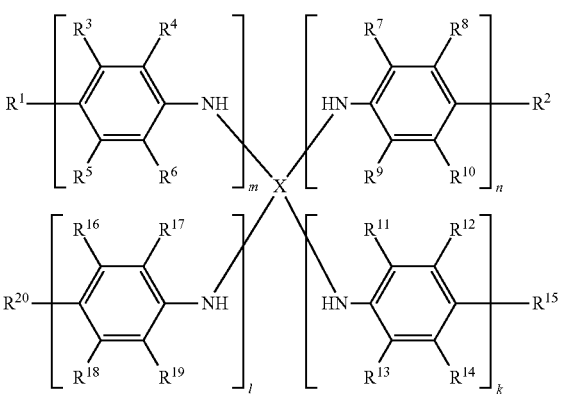

wherein
R¹ and R² independently represent a hydrogen atom, a halogen atom, a hydroxyl group, a silanol group, a thiol group, a carboxyl group, a phosphate group, a phosphoric acid ester group, an ester group, a thioester group, an amide group, a nitro group, a monovalent hydrocarbon group, an organoxy group, an organosilyl group, an organothio group, an acyl group, or a sulfone group,
R³ to R²⁰ independently represent a hydrogen atom, a halogen atom, a hydroxyl group, an amino group, a silanol group, a thiol group, a carboxyl group, a phosphate group, a phosphoric acid ester group, an ester group, a thioester group, an amide group, a nitro group, a monovalent hydrocarbon group, an organoxy group, an organoamino group, an organosilyl group, an organothio group, an acyl group, or a sulfone group,
m, n, l and k are, respectively, such integers that $1 \leq m \leq 20$, $1 \leq n \leq 20$, $1 \leq l \leq 20$ and $1 \leq k \leq 20$ are satisfied,
in formulas (1), (3), and (4), X represents a fluorinated aryl group, and
in formula (2), X' represents a fluorinated aryl group wherein the aryl group is biphenyl, binaphthyl, naphthyl, anthracene, naphthacene, terphenyl, tetraphenyl, pyridyl, bipyridyl, thiophene, bithiophene, pyrrole, bipyrrole, furan, bifuran, carbazole, phenanthroline, pyrene, quinoline, isoquinoline, pyridazine, pyrimidine, purine, acridine, pyrazine, quinoxaline, quinazoline, phthalazine, indole, benzofuran, benzothiophene, pyrazole, isoxazole, isothiazole, indazole, benzoisoxazole, benzisothiazole, imidazole, oxazole, thiazole, benzimidazole, benzoxazole, and benzthiazole.

2. An oligoaniline compound wherein a primary and/or secondary amino group existing in the compound represented by the formula (1), (2), (3) or (4) is intermolecularly added to the fluorinated aryl group of the compound represented by the formula (1), (2), (3) or (4)

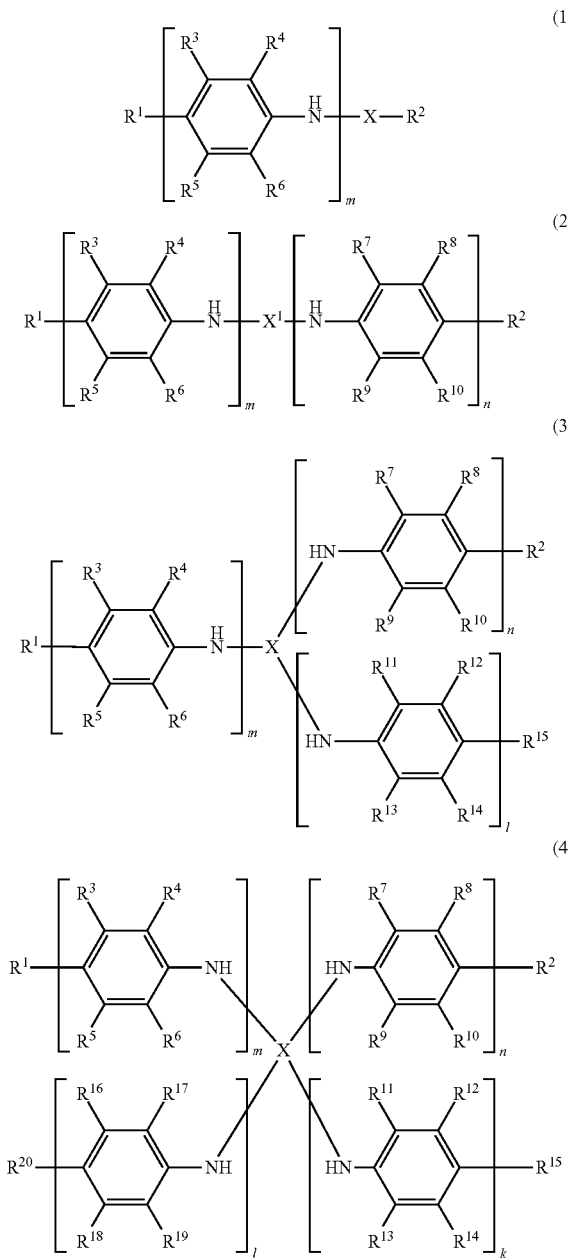

wherein $R^1$ and $R^2$ independently represent a hydrogen atom, a halogen atom, a hydroxyl group, an amino group, a silanol group, a thiol group, a carboxyl group, a phosphate group, a phosphoric acid ester group, an ester group, a thioester group, an amide group, a nitro group, a monovalent hydrocarbon group, an organoxy group, an organosilyl group, an organothio group, an acyl group, or a sulfone group, $R^3$ to $R^{20}$ independently represent a hydrogen atom, a halogen atom, a hydroxyl group, an amino group, a silanol group, a thiol group, a carboxyl group, a phosphate group, a phosphoric acid ester group, an ester group, a thioester group, an amide group, a nitro group, a monovalent hydrocarbon group, an organoxy group, an organoamino group, an organosilyl group, an organothio group, an acyl group, or a sulfone group, m, n, l and k are, respectively, such integers that $1 \leq m \leq 20$, $1 \leq n \leq 20$, $1 \leq l \leq 20$ and $1 \leq k \leq 20$ are satisfied, in formulas (1), (3), and (4), X represents a fluorinated aryl group, and in formula (2), X' represents a fluorinated aryl group wherein the aryl group is biphenyl, binaphthyl, naphthyl, anthracene, naphthacene, terphenyl, tetraphenyl, pyridyl, bipyridyl, thiophene, bithiophene, pyrrole, bipyrrole, furan, bifuran, carbazole, phenanthroline, pyrene, quinoline, isoquinoline, pyridazine, pyrimidine, purine, acridine, pyrazine, quinoxaline, quinazoline, phthalazine, indole, benzofuran, benzothiophene, pyrazole, isoxazole, isothiazole, indazole, benzoisoxazole, benzisothiazole, imidazole, oxazole, thiazole, benzimidazole, benzoxazole, and benzthiazole.

3. The oligoaniline compound as defined in claim 1 or 2, wherein X is a fluorinated biphenyl group, a fluorinated phenyl group, a fluorinated binaphthyl group or a fluorinated naphthyl group.

4. The oligoaniline compound as defined in claim 1 or 2, wherein X is a perfluorobiphenyl-derived group, a perfluorobenzene-derived group, a perfluorobinaphthyl-derived group or a perfluoronaphthalene-derived group.

5. A charge-transporting varnish comprising the oligoaniline compound defined in claim 1 or 2.

6. A charge-transporting thin film comprising the oligoaniline compound defined in claim 1 or 2.

7. A charge-transporting thin film formed from the charge-transporting varnish defined in claim 5.

8. An organic electroluminescent device comprising the charge-transporting thin film defined in claim 6.

9. A solar cell comprising the charge-transporting thin film defined in claim 6.

10. The oligoaniline compound as defined in claim 1, wherein $R^3$ to $R^{14}$ and $R^{16}$ to $R^{19}$ independently represent a hydrogen atom, a hydroxyl group, an amino group, a silanol group, a thiol group, a carboxyl group, a phosphate group, a phosphoric acid ester group, an ester group, a thioester group, an amide group, a nitro group, a monovalent hydrocarbon group, an organoxy group, an organoamino group, an organosilyl group, an organothio group, an acyl group, or a sulfone group.

11. The oligoaniline compound as defined in claim 2, wherein $R^3$ to $R^{14}$ and $R^{16}$ to $R^{19}$ independently represent a hydrogen atom, a hydroxyl group, an amino group, a silanol group, a thiol group, a carboxyl group, a phosphate group, a phosphoric acid ester group, an ester group, a thioester group, an amide group, a nitro group, a monovalent hydrocarbon group, an organoxy group, an organoamino group, an organosilyl group, an organothio group, an acyl group, or a sulfone group.

12. The oligoaniline compound as defined in claim 1 or 2, wherein X' is
- a fluorinated biphenyl group,
- a fluorinated binaphthyl group, or
- a fluorinated naphthyl group,
    - which is
- a compound represented by formula (2) as defined in claim 1 or
    - which is
- a compound wherein a primary and/or secondary amino group in a compound represented by formula (2) as defined in claim 1 is intermolecularly added to a fluorinated aryl group of a compound represented by formula (2) as defined in claim 2.

13. The oligoaniline compound as defined in claim 12, wherein X' is
- a perfluorobiphenyl-derived group,
- a perfluorobinaphthyl-derived group, or
- a perfluoronaphthalene-derived group.

* * * * *